US006964770B2

(12) United States Patent
Brubaker et al.

(10) Patent No.: US 6,964,770 B2
(45) Date of Patent: Nov. 15, 2005

(54) **RECOMBINANT PLASMID AND A METHOD OF CONTROLLING THE EFFECTS OF *YERSINIA PESTIS***

(75) Inventors: Robert R. Brubaker, Vermontville, MI (US); Vladimir L. Motin, E. Lansing, MI (US); George B. Smirnov, Moscow (RU)

(73) Assignee: Michigan State University, E. Lansing, MI (US)

( * ) Notice: Subject to any disclaimer, the term of this patent is extended or adjusted under 35 U.S.C. 154(b) by 0 days.

(21) Appl. No.: 10/694,614

(22) Filed: Oct. 27, 2003

(65) Prior Publication Data

US 2004/0126390 A1 Jul. 1, 2004

Related U.S. Application Data

(62) Division of application No. 08/302,423, filed on Sep. 8, 1994, now Pat. No. 6,638,510.

(51) Int. Cl.$^7$ ........................ A61K 39/02; A61K 39/00; C12N 15/09; C07H 21/04
(52) U.S. Cl. ............................... 424/234.1; 424/184.1; 435/69.3; 536/23.7
(58) Field of Search .......................... 424/234.1, 184.1; 435/69.3; 536/23.7

(56) References Cited

U.S. PATENT DOCUMENTS 3,137,629 A   6/1964   Cocking et al.
4,455,142 A   6/1984   Martins et al.
5,213,796 A   5/1993   Garcea et al.

OTHER PUBLICATIONS

Motin et al May 1994 Abstracts of the General Meeting of the American Society for Microbiology, vol. 94, pp 155.*
Straley et al 1986, Infect Immun; 51(2): 445–454.*
Watson et al 1988 Infect Immun. May 1988; 56(5): 1358–1363.*
Bergman et al et al 1991 Journal of Bacteriology, 173; 1607–1616.*
Injection and Immunity, "Passive Immunity To Yersiniae Mediated By Anti–Recombinant V Antigen and Protein A–V Antigen Fusion Peptide", V.L. Motin et al., Oct. 1994, vol. 62, No. 10, p. 4192–4201.
In *Virulence and Immunogenicity Of Pasteurella Pestis*, "The Effects of Loss of Different Virulence Determinants On the Virulence And . . . ", T.W. Burrows and G.A. Bacon, 1958, p. 278–291.
Microbial Pathogenesis, "Transcription of the yop regulon from Y. enterocolitica requires trans acting pYV & Chromosomal genes", G. Cornelis et al., 1987, 2:367–379.
Molecular Microbiology, "The Surface–Located YopN Protein Is Involved In Calcium Signal Transduction in *Yersinia Pseudotuberculosis*", 1991, 5(4), 977–986.
Science, vol. 249, Aug. 1990, "Protein Tyrosine Phosphatase Activity of an Essential Virulence Determinant in Yersinia", K. Guan and J.E. Dixon, p. 553–556.

(Continued)

*Primary Examiner*—Lynette R. F. Smith
*Assistant Examiner*—Padma Baskar
(74) *Attorney, Agent, or Firm*—Wilmer Cutler Pickering Hale and Dorr LLP

(57) ABSTRACT

Described is a plasmid prepared by recombinant techniques which is used to prepare a vaccine against *Y. pestis*.

3 Claims, 7 Drawing Sheets

OTHER PUBLICATIONS

"The Pigmentation of *Pasteurella Pestis* On a Defined Medium Containing Haemin", S. Jackson & T.W. Burrows, 1956, p. 570–576.

Brit. J. Exp. Path. 37:597–583, "The Virulence–Enhancing Effect Of Iron On Non–Pigmented Mutants Of Virulent Strains Of *Pasteurella Pestis*", S. Jackson and T.W. Burrows.

Infection and Immunity, Oct. 1990, vol. 58, No. 10, "YopM Inhibits Platelet Aggregation and Is Necessary for Virulence of *Yersinia Pestis* in Mice", Ka Yin Leung et al., p. 3262–3271.

In Protein Measurement With Folin Reagent, "Protein Measurement With The Folin Phenol Reagent", O.H. Lowry et al., 1931, p. 265–275.

Microbial Pathogenesis, 1987, "Modulation of the Low–Calcium Response in *Yersinia Pestis* via Plasmid–Plasmid Interaction", A.K. Sample et al. 2:442–453.

Microbial Pathogenesis, "Expression Of the Low Calcium Response In *Yersinia Pestis*", R.J. Mehigh et al., 1989, 6: 203–217.
J. of Bacteriology, Mar. 1991, "Secretion of Hybrid Proteins by the yersinia Yop Export System", p. 1677–1685.
In A.V. Naumov (ed.), Microbiology and biochemistry of particularly dangerous infections, Anti–Plague Institute "Microbe" Press, Saratov, Russia, p. 3–11.
J. of Bacteriology, Aug. 1991, vol. 173, No. 16, "Analysis of virC, an Operon Involved in the Secretion of Yop Proteins by *Yersinia enterocolitica*", p. 4994–5009.
Infection and Immunity, Sep. 1990, "Secretion of Yop Proteins by Yersiniae", T. Michiels et al., p. 2840–2849.
Analytical Biochemistry 117, 307–310 (1981) Silver Stain for Proteins in Polyacrylamide Gels: A Modified Procedure with Enhanced Uniform Sensitivity, J.H. Morrissey.
Infection and Immunity, Apr. 1983, "Vwa+ Phenotype of *Yersinia enterocolitica*", R.D. Perry and R.R. Brubaker, vol. 40, No. 1, p. 2840–2849.
Infection and Immunity, Nov. 1986, "A Low–$Ca^2$+ Response Operon Encodes the V Antigen of *Yersinia Pestis*", R.D. Perry et al., vol. 54, No. 2, p. 428–434.
Infection and Immunity, Aug. 1988, "Inhibition of Phagocytosis in *Yersinia Pseudotuberculosis:* a Virulence Plasmid–Encoded Ability Involving the Yop2b Protein", R. Rosqvist et al., p. 2139–2143.
Science, vol. 258, Nov. 1992, "A Surface Protease and the Invasive Charactger of Plague", O.A. Sodeinde et al. p. 1004–1007.
Infection and Immunity, Apr. 1982, vol. 36, No. 1, "Localization in *Yersinia Pestis* of Peptides Associated With Virulence", S.C. Straley and R.R. Brubaker, p. 129–135.
Infections and Immunity, Apr. 1989, vol. 57, No. 4, "Differential Clearance and Host–Pathogen Interactions of $YopE^-$and $YopK^-YopL^-$*Yersinia Pestis* in BALB/c Mice", S.C. Straley et al., p. 1200–1210.
Applied Microbiology, Nov. 1969, vol. 18, No. 5, "Congo Red–Agar Plating Medium for Detecting Pigmentation in *Pasteurella Pestis*", M.J. Surgalla and E.D. Beesley, p. 834–837.
J. of Bacteriology, Sep. 1979, vol. 139, No. 3, "Consequences of $Ca^2$ + Deficiency on Macromolecular Synthesis and Adenylate Energy Charge in *Yersinia Pestis*", R.J. Zahorchhak et al., p. 792–799.
Bergman, T., et al, "Analysis of the V antigen 1crGVH–yopBD operon of *Yersinia Pseudotuberculosis:* Evidence of a regulatory role of LcrH and LcrV", J. Bacteriol. 173:1607–1616, 1991.
Bolin, I., and H. Wolf–Watz. "The plasmid–encoded Yop2b protein of *Yersinia pseudotuberculosis* is a virulence determinat regulated by calcium and temperature at transcriptional level". Mol. Microbiol. 2:237–245, 1988.
Brubaker, R.R. "The V antigen of yersiniae—an overview". *Contrib. Microbiol. Immunol.,* 12: 127–133, 1991.
Brubaker, R.R. 1991. "Factors promoting acute and chronic diseases caused by yersiniae". Clin. Microbial. Rev. 4:309–324.
Brubaker, R.R., A.K. Sample, D.–Z. Yu, R.J. Zahorchak, P.C. Hu, and J.M. Fowler. 1987. "Proteolysis of V antigen from *Yersinia pestis*". Microb. Pathog. 2:49–62.
Burrows, T.W. 1956. "An antigen determining virulence in *Pasteurella pestis.*" Nature (London) 177:426–427.
Burrows, T.W., et al. 1958. "The Basis of virulence in *Pasteurella pestis*: an antigen determining virulence". Brit. J. Exp. Pathol. 37–481–493.
Burrows, T.W., et al, 1960. "V and W antigens in strains of Pasteurella pseudo–tuberculosis", Br. J. Exp. Pathol. 41:38–44.
Carter, P.B., et al. 1980. "Plague virulence antigens from *Yersinia enterocolitica*" Infect. Immun. 28:638–640.
Fetherston, J.D., et al. 1992. "Loss of the pigmentation phenotype in *Yersinia pestis* is due to the spontaneous deletion of 102kb, etc." Mol. Micribiol 6:2693–2704.
Charnetzky, W.T., et al. 1982. "RNA synthesis in *Yersinia pestis* during growth restriction in calcium deficient medium." J. Bacteriol. 149:1089–1095.
Gandecha, A.R., et al. 1992. "Production and secretion of a bifunctional staph–lococcal protein A: antiphytochrome single–chain Fv fusion protein in *Escherichia coli*" Gene 122:361–365.
Grodberg, J., and J.J. Dunn 1988 "ompT encodes the *Escherichia coli* outer membrane protease that cleaves 17 RNA polymerase during purification". J. Bacteriol. 170:1245–1253.
Hakansson, S., et al 1993 "YopB and YopD constitute a novel class of Yersinia Yop proteins." Infect. Immun. 61:71–80.
Leung,K.Y., and S.C. Straley 1989. "The yopM gne of *Yersinia pestis* encodes an released protein having homology with the human platelet surface protein GPIb", J. Bacteriol. 171:4623–4623.
Lawton, W.D., et al. 1963. "Biosynthesis and purification of V and W antigen in *Pasteurella pestis.*" J. Immunol. 91:179–184.
Lucier, T.A., and R.R. Brubaker. 1992. "Determination of genome size, macrorestriction pattern polymorphism, and nonpigmentation–specific deletion in *Yersinia pestis* by pulsed–filed gel electrophoresis." J. Bacteriol. 174:2078–2086.
Lowenadler, B., et al 1987. "A gene fusion system for generating antibodies against short peptides." Gene 58:87–97.
Mehigh, R.J. and R.R. Brubaker. 1993. "Major stable peptides of *Yersinia pestis* synthesized during the low–calcium response". Infect. Immun. 61:13–22.
Michiels, T., and G. Cornelis. 1988. "Nucleotide sequence and transcription analysis of yop51 from *Yersinia enterocolitica* W22703" Microb. Pathog. 5:449–459.

Motin, V.L., et al. 1991. "The difference in the *lcrV*–sequences between *Y. pestis* and *Y. pseudotuberculosis,* etc." Microb. Pathog. 12:165–175.

Mulder, B., et al. 1989. "Identification of additional virulence determinants of the pYV plasmid of *Yersinia enterocolitica* W227" Infect. Immun. 57:2534–2541.

Nakajima, R., and R. R. Brubaker. 1993. "Association between virulence of *Yersinia pestis* and suppression of gamma interferon and tumor necrosis factor alpha." *Infect. Immun.* 61:23–31.

Nilsson, B., L. Abrahmsen, and H. Uhlen. 1985. "Immobilization and purification of enzymes with staphylococcal protein A gene fusion vectors." EMBO J. 4:1075–1080.

Price, S.B., et al. "The V antigen is a regulator protein necessary for the $Ca^{2+}$–dependent growth, etc." J. Bacteriol. 173:2649.

Reisner, B.S. and S.C. Straley. 1992. "*Yersinia pestis* YopM: Thrombin binding and overexpression." Infect. Immun. 60:5242–5252.

Price, S.B., et al. 1989. "Molecular analysis of lcrGVH, the V operon of *Yersinia pestis*." J. Bacteriol. 171:5646–5653.

Rosqvist, R., et al. 1990. "The Cytotoxic Yop E of Yersinia obstructs the primary host defense." Mol. Microbiol. 4:657.

Rosqvist, R., et al. 1991. "Intracellular targeting of the Yersinia YopE cytotoxin in mammalian cells induces actin microfilament disruption." Infect. Immun. 59:4562–4569.

Sato, K., R. Nakamima, et al. 1991. "Preparation of monoclonal antibody to V Antigen from *Yersinia pestis*." Contrib. Microbiol. Immunol. 12:225–229.

Sample, A.K., et al. 1987. "Posttranslational regulation of Lcr plasmid–mediated peptides in pesticinogenic *Yersinia pestis.*" Microb. Pathog. 3:239–249.

Straley, S.C., and W.S. Bowmer. 1986. "Virulence genes regulated at the transcriptional level by $Ca^{2+}$ in *Yersinia pestis* include structural genes for outer membrane proteins." Infect. Immun. 51:445–454.

Sodeinde, O.A., et al. 1988. "Plasminogen activator/coagulase gene of *Yersinia pestis* is responsible for degradation of plasmid–encoded outer membrane proteins." Infect. Immun. 56:2749–2752.

Une, T., and R.R. Brubaker. 1984. "Roles of V antigen in promoting virulence and immunity in yersiniae." J. Immunol. 133:2226–2230.

Une, T., R. Nakajima, and R.R. Brubaker. 1986. "Roles of V antigen in promoting virulence in Yersinia." Contrib. Microbiol. Immunol. 9:179–185.

Uhlen, M. B. Guss, et al. 1984. "Complete sequence of the staphylococcal gene encoding protein A." J. Biol. Chem. 259:1695–1702.

Une, T., and R.R. Brubaker. 1984. "In vivo comparison of avirulent Vwa and Pgm or Pst' phenotypes of yersiniae." Infect. Immun. 43:895–900.

\* cited by examiner

FIG. 5

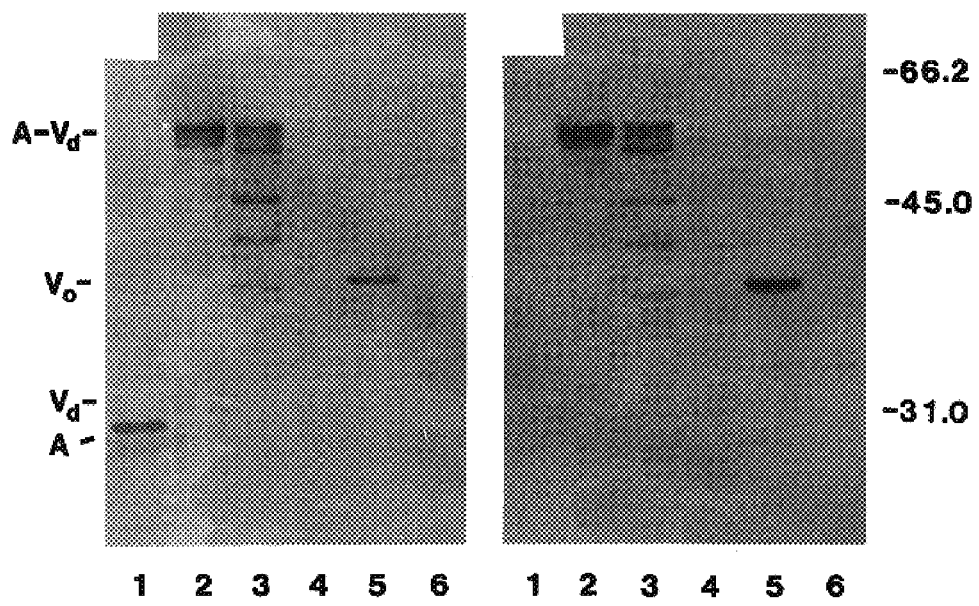

RECOMBINANT PLASMID AND A METHOD OF CONTROLLING THE EFFECTS OF YERSINIA PESTIS

CROSS-REFERENCE TO RELATED APPLICATIONS

The present application is a divisional of U.S. application Ser. No. 08/302,423, filed Sep. 8, 1994, now U.S. Pat. No. 6,638,510 B1.

LICENSING RIGHTS

The United States government may have licensing rights to this application in accordance with U.S. Public Health Service Grant AI 19353.

TECHNICAL FIELD

The present invention is concerned with bubonic plague caused by *Yersinia pestis* and vaccines for treating same.

BACKGROUND ART

Experimental plague in mice, caused by *Yersinia pestis*, is mediated by two distinct types of virulence factors. Members of the first category serve as whole animal or tissue invasins by promoting dissemination of the organisms into visceral organs following infection by peripheral routes of injection (e.g. intraperitoneal or subcutaneous). Mutants lacking one or more tissue invasins can exhibit significant reduction in virulent (50% lethal dose>$10^2$ to $10^7$ bacteria) by peripheral administration but retain essentially full lethality (50% lethal dose ca. $10^2$ bacteria) upon intravenous injection (4). Examples of this group (6, 16, 48) include the outer membrane (46) plasminogen activator (1) mediated by a ca. 10 kb pesticin or Pst plasmid (12, 41) and a series of iron repressible outer membrane peptides (10, 40) encoded by a delectable ca. 100 kb chromosomal segment (11, 22).

Examples of the second category function to promote lethality following infection by the intravenous route, known to facilitate immediate transport of the bacteria to favored niches within visceral organs (4). Mutational loss of these lethal factors causes qualitative (intravenous 50% lethal dose>$10^7$ bacteria) decreases in virulence. Included in this group are certain ca. 70 kb low calcium response or Lcr plasmid encoded proteins: V antigen (9, 27), others termed Yops (18, 19, 33, 47): YopE (23, 35, 43, 44, 47), YopH (3, 34, 44), and probably YpkA (13), as well as chromosomally encoded antigen 4 or pH 6 antigen (20) and possibly the murine exotoxin encoded by the ca. 100 kb Tox plasmid (32.). Considerable effort has been spent in study of the regulation, processing, and delivery of these proteins to host cells (2, 15, 26, 28, 30, 31, 35).

The effectiveness of the immune response directed against members of the second category of virulence factors has only been reported for V antigen. Some (17, 24, 27, 39, 49, 50) but not all (5) antibodies directed against this 37 kDa exported (8, 17, 43, 44) protein provided significant passive protection against experimental plague in mice. This effect was associated with release of a potent immunosuppressive block preventing both synthesis of cytokines (27) and formation of protective granulomas (50).

Plague vaccines have been identified in U.S. Pat. No. 3,137,629. The patent describes a process for producing killed plague vaccines which immunizes mice and guinea pigs by growing *Pasteurella pestis*, killing the strain through mechanical action and solubilizing the extract in strong alkaline solution, and then preparing parenteral vaccine by reducing the pH value of the soluble *P. pestis* antigenic solution to a neutral pH.

It is an object of the present invention to prepare a plasmid by recombinant techniques.

It is another object of the present invention to prepare an antigen encoded by the recombinant plasmid.

It is a further object of the present invention to control the effect *Y. pestis* has on mammals by utilizing a vaccine to *Y. pestis* constituting the antigen noted above.

SUMMARY OF THE INVENTION

The present invention is concerned with a plasmid prepared by recombinant techniques having the construct shown in FIG. 1.

Also described is a protein encoded by the plasmid shown in FIG. 1, capable of inducing a protective antibody response.

The invention is further concerned with a method of controlling the effects of *Y. pestis* in mammals comprising the steps of:

a) providing a vaccine comprised of the protein encoded by the construct of FIG. 1; and b) treating a mammal in need thereof with an effective anti-*Y. pestis* amount of the vaccine.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5 is a chart of antiserum for passive immunization against native V antigen, recombinant V antigen, recombinant protein A-V antigen fusion and recombinant protein A;

FIG. 6 are immunoblots prepared with rabbit anti-native V antigen (A) or mouse monoclonal 17A5.1 anti-V antigen (B) directed against truncated protein A (PA) (lane 1), protein A-V antigen fusion peptide (PAV) (lane 2), PAV partially hydrolyzed by formic acid (lane 3), PAV partially hydrolyzed by formic acid and passed through the IgG Sepharose 6FF column (lane 4), whole Lcr⁺ cells of *Yersinia pestis* KIM (lane 5), and whole LCR⁻ cells of *Y. pestis* KIM (lane 6); A-$V_d$, $V_o$, $V_d$, and A indicate the positions of PAV, native V antigen (37 Kda), truncated V antigen (29.5 kDa), and truncated Protein A, respectively. Human γ-globulin was used to block nonspecific reactions of monoclonal antibodies against IgG-binding domains of Protein A (26)

DESCRIPTION OF THE BEST MODE

Figure 1A:
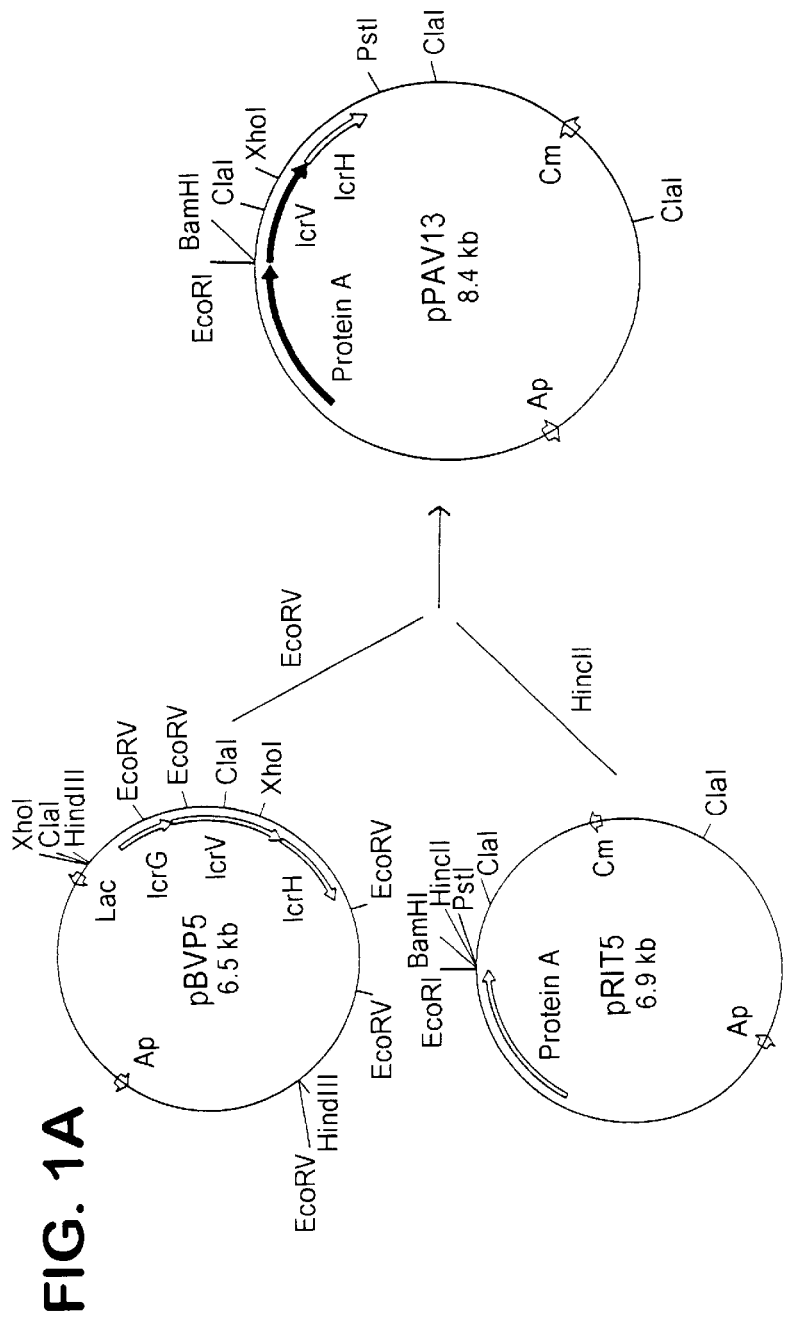
FIG. 1A is a scheme of construction of a recombinant plasmid formed by joining the DNA encoding the signal sequence and IgG binding domains of staphylococcal protein A and that of all but the 201 N-terminal base pairs of *Y. pestis* V antigen; antibody to which is capable of effecting immunological treatment against *Y. pestis*.

The medically significant yersiniae (*Yersinia pestis, Y. pseudotuberculosis*, and *Y. enterocolitica*) are known to share a ca. 70 kb low calcium response (Lcr) plasmid that mediates restriction of vegetative growth at 37° C. in $Ca^{2+}$-deficient media while promoting selective synthesis of virulence factors including V antigen. The latter, encoded by lcrV on the Lcr plasmid, is established as a 37 kDa protective antigen capable of undergoing possible autoproteolytic hydrolysis. In this study, lcrV of *Y. pestis* was cloned under control of the strong tac promoter into protease-deficient *Escherichia coli* BL21. The resulting recombinant V antigen, like native V antigen, underwent degradation during purification yielding major peptides of ca. 36,35,34 and 32 to 29 kDa. Rabbit γ-globulin raised against this mixture of cleavage products provided partial but significant protection against 10 minimal lethal doses (MLD) of the three species. To stabilize V antigen and facilitate its purification, plasmid pPAV13 was constructed so as to encode a fusion of lcrV and the structural gene for staphylococcal protein A (e.g. all but the first 67 N-terminal amino acids of V antigen and the signal sequence plus IgG binding domains but not cell-wall associated region of protein A). The resulting protein A-V antigen fusion peptide (PAV) could be purified to homogeneity in one step IgG affinity chromatography and was found to be stable thereafter. Rabbit polyclonal γ-globulin directed against PAV provided substantial passive immunity against 10 MLD of *Y. pestis* and *Y. pseudotuberculosis* but was ineffective against *Y. enterocolitica*.

The vaccine as described herein is generally applied by parenteral administration to mammals in need thereof.

The vaccine of the present invention is generally administered in the form of pharmaceutical compositions comprising a pharmaceutically acceptable vehicle or diluent. Such compositions are generally formulated in a conventional manner utilizing liquid vehicles or diluents as appropriate to the mode of desired administration: for parenteral administration (e.g. intramuscular, intravenous, intradermal), in the form of injectable solutions or suspensions, and the like. For use as a vaccine in a mammal, including man, it is given in an amount of about 0.5–100 mg/kg.

The vaccine described herein is used in conjunction with normal pharmaceutical excipients to facilitate storage and use.

The present invention is further illustrated by the following examples. These examples are provided to aid in understanding of the invention and not to be construed as a limitation thereof.

Materials and Methods

Bacteria. *Escherichia coli* K-12 XL1-Blue {recA1 endA1 gyrA96 thi-1 hsdR17 supE44 relA1 lac [F' proAB lacI$^q$ZΔM15Tn10 (tet$^r$)]} (Stratagene, La Jolla, Calif.) was used as a host for genetic engineering manipulations. Protease-deficient *E. coli* BL21 {F⁻ ompT lon $r_B$- $m_B$-} (Novagen, Madison, Wis.) was used for expression of cloned genes (17). Mice passively immunized with the products of cloned genes were challenged with wild type cells of *Y. enterocolitica* WA (10) or *Y. pseudotuberculosis* PB1/+ (9). This purpose was accomplished with *Y. pestis* KIM by use of a nonpigmented mutant (20,59) known to lack a spontaneously deletable ca. 100 kb chromosomal fragment encoding functions of iron transport and storage (14,28); the isolate in question retained all other known chromosomally encoded virulence functions as well as the Tox, Lcr, and Pst plasmids (13,57). Nonpigmented mutants of this phenotypic background are virulent in mice by the intravenous (50% lethal dose ca. 10 bacteria, 61) but not by peripheral routes of infection (50% lethal dose>$10^7$ bacteria, 21).

Plasmids. Salient features of plasmids used in this study are shown in Table 1. The vector pKK223-2 containing the tac promoter (Pharmacia, Uppsala, Sweden) was used to express a portion of the lcrGVH-yopBD operon of *Y. pestis* 358 (22) as described below. The vector pRIT5 (Pharmacia) encoding the sequence of Protein A of *Staphylococcus aureus* was used for preparation of gene fusions. The recombinant plasmid pBVP5 containing the lcrGVH-YopBD operon of *Y. pseudotuberculosis* (38) served as the source of lcrV in preparing this construction.

TABLE 1

Characterization of Deletional Variants of HindIII Fragment From The lcrGVH-yopBD Operon of Yersinia pseudotuberculosis 995.

| Encoding Plasmid | Size Of Fragment | Operon | Designation Of V Antigen | Size of V Antigen (kDa) |
|---|---|---|---|---|
| pBVP5 | ~3,500 | lcrGVHyopBD | $V_0$ | 37.3 |
| pBVP513D | 2,184 | lcrGVH | $V_0$ | 37.3 |
| pBVP53D | 1,484 | lcrGV$_1$ | $V_1$ | 31.5 |
| pBVP514D | 1,160 | lcrGV$_2$ | $V_2$ | 19.3 |
| pBVP515D | 878 | lcrGV$_3$ | $V_3$ | 8.5 |
| pBVP58D | 705 | lcrGV$_4$ | $V_4$ | 2.0 |
| pBVP55D | 546 | lcrG$_1$ | — | — |

Molecular weights of truncated V antigens were calculated from the deletion terminus as determined by nucleotide sequencing; actual values may be slightly greater due to translational overruns into the vector polylinker region.

DNA Methods. The preparation of plasmid DNA, digestion with restriction enzymes, ligation, and transformation of *E. coli* were undertaken essentially as described by Maniatis et al (29). The 3.5 kb HindIII fragment of the Lcr plasmid of *Y. pestis* 358 (22,38) was introduced into expression vector pKK223-3. The resulting recombinant plasmid pKVE14 was then selected where the direction of transcription of the lcrGVH sequence corresponds to the direction of action of the tac promoter.

Figure 1B:
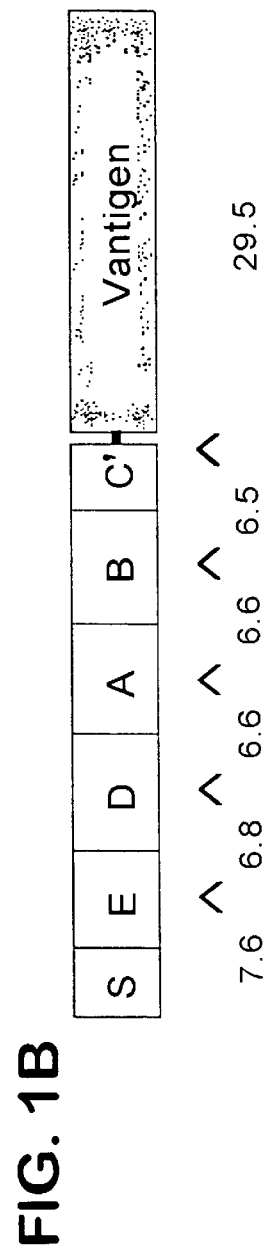
FIG. 1B cites a restriction endonuclease attack on the V antigen.

The schema used to construct pPAV13 containing a hybrid gene encoding a portion of Protein A of *S. aureus* and lcrV of *Y. pseudotuberculosis* is shown in FIG. 1A. The 1.5 kb EcoRV fragment of recombinant plasmid pBVP5 (38) was introduced into the vector pRIT5 encoding truncated Protein A (PA). The latter, either alone or fused with V antigen, maintained its signal sequence and most IgG-binding domains but lost the region mediating association with the bacterial cell surface (41,42) (FIG. 1B). PA does not contain cysteine and is thus unable to form disulfide bridges between itself and a hybrid domain (60). As a consequence of this fusion, lcrV lost 201 bp which thus deleted the first 67 amino acids comprising the N-terminal portion of V antigen. The resulting Protein A-V antigen fusion peptide (PAV) thus contained 305 N-terminal amino acids from Protein A and 259 C-terminal amino acids from V antigen (FIG. 1B).

Purification of Recombinant V Antigen. Cells of *E. coli* BL21 (pKVE14) were grown in fermenters as described previously (5) in medium containing 3% Sheffield NZ Amine, Type A (a pancreatic hydrolysate of casein which contains mixed amino acids and peptides and is used to facilitate the growth of bacteria) (Kraft, Inc., Memphis, Tenn.), 0.5% NaCl, 1% lactose, and ampicillin (100 µg/ml) at 37° C. and harvested by centrifugation (10,000×g for 15 min) at an optical density (620 nm) of about 1.2. After disruption in a French pressure cell (SLM Instruments, Inc., Urbana, Ill.) and removal of insoluble matter by centrifugation (10,000×g for 30 min), V antigen was subjected to purification by an established procedure (5). The method involved use of hydrophobic interaction chromatography with phenyl-Sepharose CL-4B (Pharmacia), ion exchange chromatography with DEAE cellulose (Whatman Inc., Clifton, J.J.), gel filtration chromatography with Sephacryl S-300SF (trademark of Pharmacia Biotechnology Group for acrylic resin for chromatograhic separation of proteins), and Bio-Gel HTP (trademark of Bio-Rad, Richmond, Calif., for calcium hydroxyapatite chromatography). The original procedure was supplemented by a second chromatographic separation of DEAE cellulose (linear gradient from 0.35 M NaCl) in order to remove high molecular weight material peculiar to *E. coli.*

Preparation of PA and PAV. Cells of *E. coli* transformed with pPAV13 or PRIT5 were grown to late log phase at 37° C. in Luria broth containing ampicillin (50 µ/ml). Purification of these recombinant proteins was accomplished by affinity chromatography on IgG Sepharose 6FF (Pharmacia) according to directions supplied by the manufacturer. Briefly, the procedure involved harvesting the organisms by centrifugation (10,000×g for 15 min) with resuspension at a ca. 10-fold increase in number in 0.01 M Tris.HCl, pH 8.0 (column buffer). Lysis was accomplished by addition of lysozyme (5 mg/ml) and, after incubation for 1 h, further addition of Triton X-100 (trademark of Rohm & Haas Co. for a nonionic detergent comprised of octyl phenoxy polyethoxy ethanol having an HLB: $13.5_j$ (0.1%) whereupon incubation was continued for 3 to 4 h. After clarification by centrifugation (10,000×g for 30 min), samples of 400 ml of the resulting enriched periplasm were passed through a column (10×100 mm) containing a 10 ml packed volume of affinity resin that selectively bound PA or PAV. After addition and elution of 10 void volumes of column buffer to remove contaminating matter, the recombinant proteins were eluted with 0.2 M acetic acid (ca. pH 3.4), immediately frozen, and then lyophilized. Resulting purified PA and PAV were then used directly for qualitative analysis and immunization.

Acid Hydrolysis of PAV. Purified PAV was treated with 70% formic acid for 20 h at 30° C. to cleave the four labile Asp-Pro peptide bonds within the Protein A domain (60) and the additional site located at the junction with V antigen (41) (FIG. 1B). After dialysis against column buffer, the partial hydrolysate was again passed through the IgG Sepharose 6FF column as described above. In this case, the V antigen moiety plus fragments of PA lacking IgG binding sites were immediately eluted whereas residual unhydrolyzed PAV remained bound to the affinity resin.

Antisera. The same lot of refined rabbit polyclonal anti-V antigen characterized previously (40) was used as a positive immunological control. Monoclonal antibodies directed against V antigen have been defined (3). These reagents consisted of two groups: monoclonals 3A4.1, 17A5.1. and 17A4.6 that reacted with nonconformational epitopes located within the last 50 amino acids comprising the C-terminal part of V antigen (amino acids 276 to 326) and monoclonal 15A4.8 that reacted with an internal nonconformational epitope located between amino acids 168 to 275 (37).

Rabbit polyclonal antisera was raised against PA and PAV with Freund's adjuvant as described previously (62). Titer-Max™ adjuvant (Hunter's TiterMax #R-1, CytRx Corp., Norcross, Ga.) was used to immunize rabbits against recombinant V antigen plus its degradation products purified from *E. coli* BL21 (pKVE14). Antisera prepared against recombinant V antigen or fusion proteins were not absorbed with material from Lcr⁻ bacteria although highly purified γ-globulin was isolated from these reagents as described previously (62). Antisera raised against V antigen purified from *Y. pestis* or *E. coli* BL21(pKVE14) is termed anti-native V antigen or anti-recombinant V antigen, respectively.

Immunoblotting. Alkaline phosphatase conjugated with anti-rabbit or anti-mouse IgG (Sigma Chemical Co., St. Louis, Mo.) were used as secondary antibodies in immunoblotting by procedures essentially identical to those already defined (51,52). In order to prevent nonspecific reactions of antibodies with PA and PAV, the nitrocellulose filter was first blocked with 5% fetal calf serum as usual and then incubated overnight in a solution of 1% normal human γ-globulin (Calbiochem, San Diego, Calif.). Human γ-globulin (0.5%) was also added to solutions of primary and secondary antibodies (26). In addition, Fc-specific anti-mouse IgG (A-1418, Sigma) was used as a secondary antibody during immunoblotting of fusion proteins and their derivatives with monoclonal antibodies.

Passive Immunity. The ability of highly purified γ-globulin obtained from unabsorbed rabbit polyclonal antisera raised against recombinant V antigen, PA, and PAV to provide passive immunity was assayed by defined methods (40,62). Briefly, this procedure involved intravenous injection of 10 minimum lethal doses (MLD) of *Y. pestis* ($10^2$ bacteria), *Y. pseudotuberculosis* ($10^2$ bacteria), or *Y. enterocolitica* ($10^3$ bacteria) followed by intravenous administration of either 100 µg or 500 µg of purified γ-globulins on postinfection days 1, 3, and 5.

Miscellaneous. Peptides were located in sodium dodecyl sulfate-polyacrylamide gel electrophoresis gels, prepared as defined previously (51,52), by silver staining (36). Soluble protein was determined by the method of Lowry et al. (27).

Results

Degradation of Recombinant V Antigen. Recombinant plasmid pKVE14 containing the lcrGVH-ypoBD operon of *Y. pestis* under control of the tac promoter was transferred into protease-deficient *E. coli* BL21. After growth in fermenters, the bacteria were disrupted and the resulting extract was used to prepare nearly homogenous recombinant V antigen using a method established for $Ca^{2+}$-starved cells of *Y. pestis* (5). An additional step involving a second separation with DEAE cellulose was necessary to eliminate major higher molecular weight proteins present in *E. coli* cytoplasm.

The initial specific activity of recombinant V antigen was almost 5-fold greater than that obtained from *Y. pestis* starved for $Ca^{2+}$ (5). Nevertheless, significant loss of precipitin activity occurred during every step of purification (Table 2). This phenomenon, as judged by a silver-stained extended lane gel (FIG. 2), reflected gradual loss of the native 37 kDa form with emergence of ca. 36 kDa, 32 kDa, and possibly smaller peptides. Analysis by immunoblotting was undertaken to prove that these new peptides shared epitopes with and thus arose from native V antigen. Use of rabbit polyclonal anti-native V Antigen (FIG. 3A) or mouse monoclonal antibody 15A4.8, directed against a centrally located epitope (FIG. 3B), demonstrated emergence of ca. 36, 35, and 34 kDa degradation products early during the course of purification with later appearance of a series of smaller fragments ranging from 32 to 29 kDa. The latter were not recognized by mouse monoclonal antibody 3A4.1 directed against an epitope located near the C-terminal end (FIG. 3C). These findings indicate that recombinant V antigen produced in protease-deficient *E. coli* BL21 undergoes evident spontaneous degradation in a manner similar to that observed from native V antigen expressed in *Y. pestis* (5). Furthermore, patterns observed upon immunoblotting with monoclonal antibodies indicate that the C-terminal portion of V is involved in this process.

specific immunoblots described below. PA and PAV were purified in one step with IgG Sepharose 6FF and then analyzed by immunoblotting. Anti-native V antigen reacted nonspecifically with PA (FIG. 6A, lane 1) and both specifically and nonspecifically with PAV (FIG. 6A, lane 2). Proof that the salient peptides shown in lanes 2, 3, and 4 of FIG. 6A reacted specifically rather than nonspecifically with anti-native V antigen was obtained by blocking PA with human γ-globulin and then immunoblotting with monoclonal anti-V antigen. This process prevented visualization of PA (FIG. 6B, lane 1) thus demonstrating that the remaining detectable bands represent a specific interaction with an epitope of V antigen. Multiple bands appearing in samples of both PA and PAV (FIG. 6A, lanes 1, 2) reflect accumulation in the periplasm of *E. coli* BL21 of the synthesized PA domain in both native and degraded forms as described by others (16). To prove that the V antigen domain of the fusion protein was stable, a sample of purified PAV was hydrolyzed with 70% formic acid to cleave acid labile Asp-Pro sites defined in FIG. 1B, neutralized, and then applied to the affinity column. Essentially pure truncated V antigen ($V_d$) emerged immediately (FIG. 6, lane 4); the absence of multiple bands in this sample provides evidence for the stability of V antigen within PAV.

Stability of PAV. The number of total units of near-homogenous PAV recovered after chromatography on IgG

TABLE 2

Purification Of Recombinant V Antigen From A Cell-Free Extract Of *Escherichia coli* BL21 (pKVE14)

| Preparation | Vol. (ml) | Protein (mg/ml) | Total Protein (mg) | V Antigen (U/ml) | Total V-antigen (U) | Specific Activity | % Recovery |
| --- | --- | --- | --- | --- | --- | --- | --- |
| Crude Extract | 200 | 26 | 5,200 | 280 | 56,000 | 11 | (100) |
| Phenyl-Sepharose CL-4B | 220 | 1.6 | 350 | 140 | 30,800 | 88 | 55 |
| DEAE Cellulose | 40 | 1.5 | 60 | 170 | 6,800 | 113 | 12.1 |
| Sephacryl S300SF | 24 | 0.7 | 17 | 140 | 3,360 | 200 | 6.0 |
| Ca Hydroxylapatite | 35 | 0.25 | 8.8 | 50 | 1,750 | 200 | 3.1 |
| DEAE Cellulose | 18 | 0.1 | 1.8 | 15 | 270 | 150 | 0.5 |

The unit of V antigen was defined as the reciprocal of the highest dilution capable of forming a visible precipitate against a standardized lot of rabbit polyclonal monospecific antiserum by diffusion in agar under conditions described previously (Lawton et al, 1963; Brubaker et al., 1987).

Figure 4A:
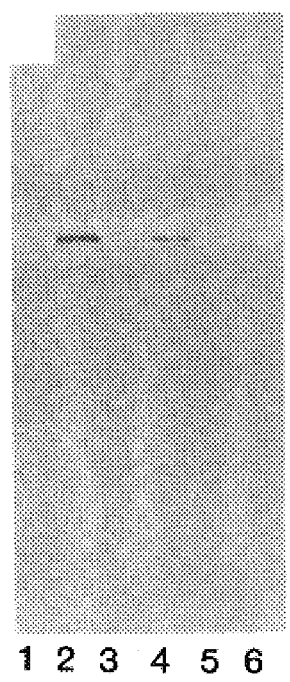
FIG. 4 are immunoblots prepared with rabbit anti-native V antigen purified from *Y. pestis* KIM (A), anti-recombinant V antigen (B), anti-protein A-V antigen fusion protein (C), and anti-Protein A (D) directed against $Ca^{2+}$-starved whole Lcr⁻ cells of *Y. pestis* KIM (lane 1), Lcr⁺ cells of *Y. pestis* KIM (lane 2), Lcr⁻ cells of *Y. pseudotuberculosis* PB1 (lane 3), Lcr⁺ cells of *Y. pseudotuberculosis* PB1 (lane 4), Lcr⁻ cells of *Y. enterocolitica* WA (lane 5), and Lcr⁺ cells of *Y. enterocolitica* WA (lane 6)
Figure 4B:
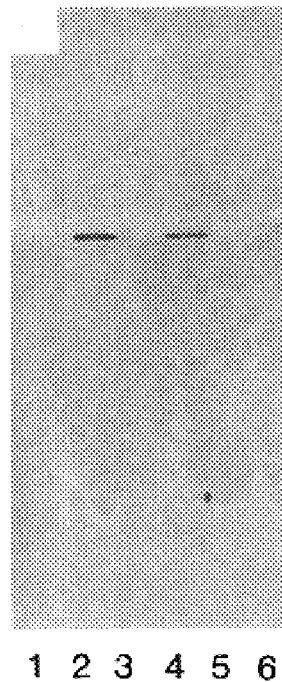
Figure 5:
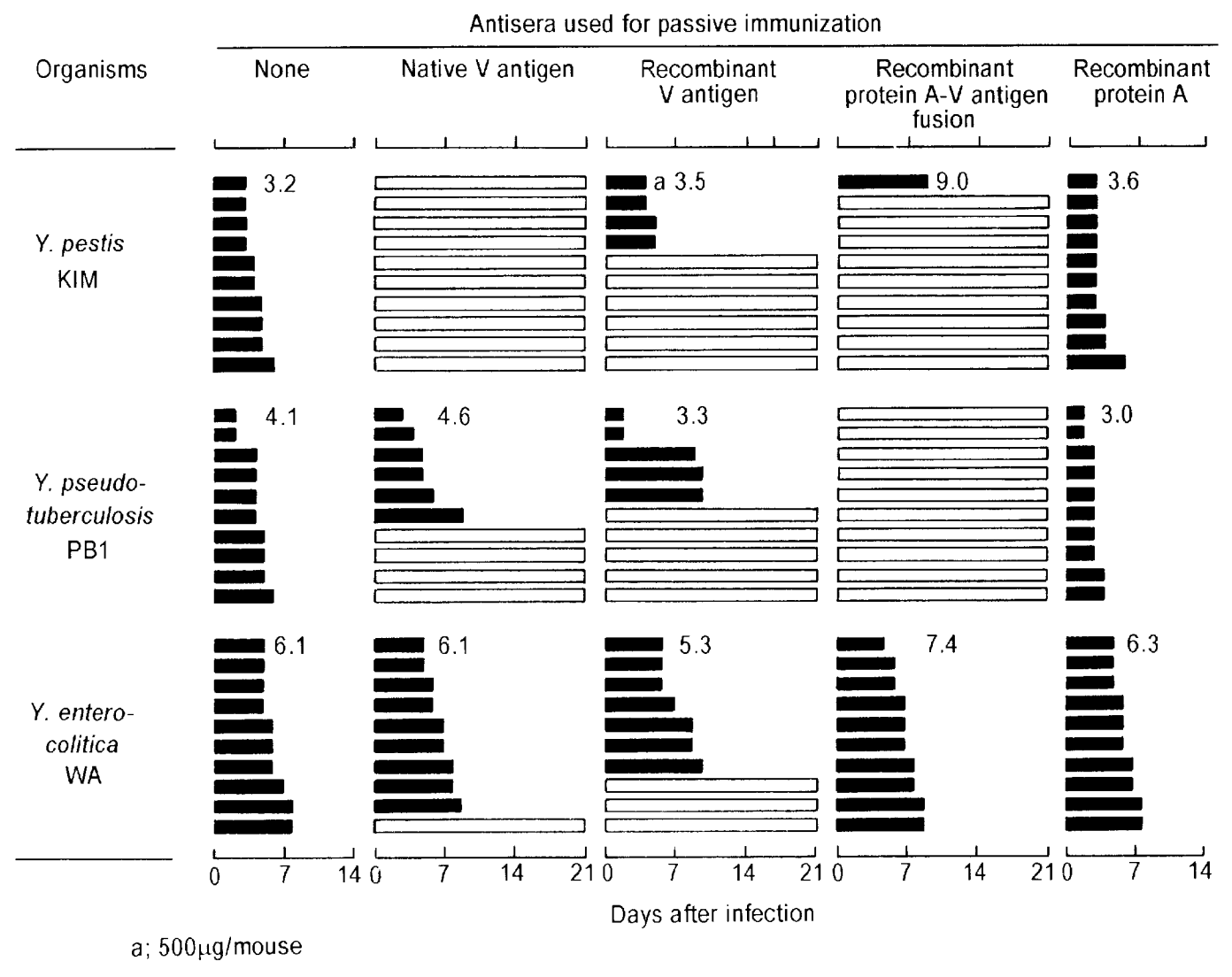

Passive Immunity Mediated by Anti-recombinant V Antigen. A portion of the purified lot of recombinant V antigen described above was used to immunize rabbits. Immunoblots of the resulting unabsorbed antisera (FIG. 4B) and control absorbed anti-native V antigen (FIG. 4A) versus $Ca^{2+}$-starved whole yersiniae were identical indicating that the reagent was monospecific. Both antisera were tested for ability to confer passive immunity against intravenous infection with yersiniae. As shown in FIG. 5, the control anti-native V antigen provided complete, partial, and insignificant protection against *Y. pestis, Y. pseudotuberculosis*, and *Y. enterocolitica*, respectively. Antirecombinant V antigen promoted a similar degree of passive immunity except that that directed against *Y. pestis* was not absolute.

Characterization of PA and PAV. Additional constructions encoding truncated staphylococcal Protein A either alone or fused with V antigen (FIG. 1) were found, after transformation into *E. coli* BL21, to promote significant synthesis of PA and PAV, respectively as judged by intensity of the Sepharose 6FF was always essentially identical to that present in the crude extract applied to the affinity column. No significant loss of purified PAV occurred during storage in 0.01 M Tris. HCl, pH 7.8 for 1 week at 4° C.

Figure 3A:
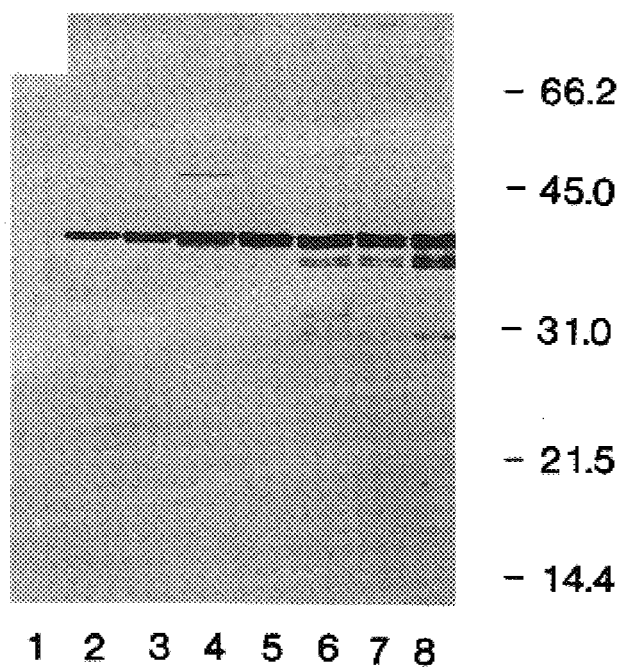
FIG. 3 are immunoblots prepared with rabbit polyclonal anti-V antigen (A) mouse monoclonal anti-V antigen 15A4.8 (B) and mouse monoclonal anti-V antigen 3A4.1 (C) directed against whole cells of *E. coli* containing the vector plasmid pKK223-3 (lane 1) or recombinant plasmid pKVE14 (lane 2)
Figures 3B, 3C:
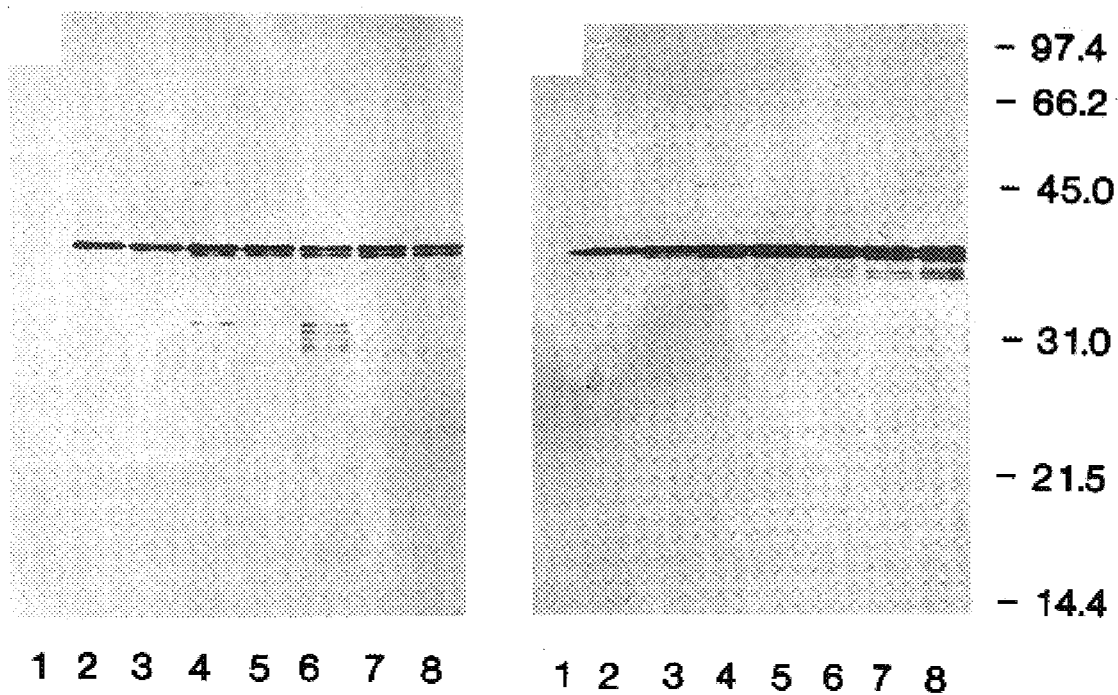
Figure 4C:
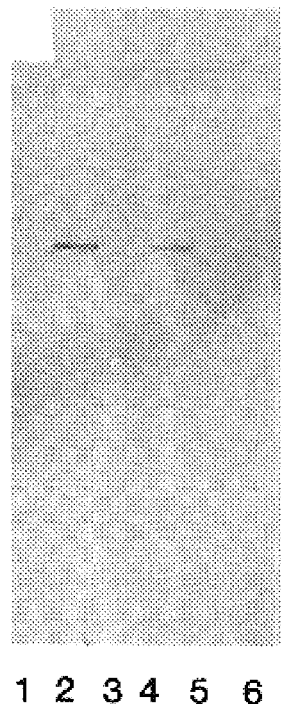
Figure 4D:
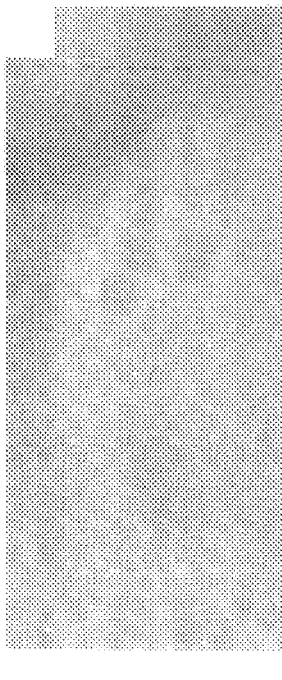
Figure 7A:
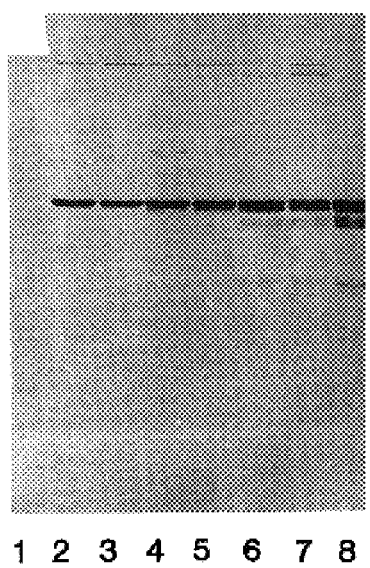
FIG. 7 are immunoblots prepared with rabbit anti-protein A-V antigen fusion peptide (A) and anti-truncated protein A (B) directed against whole cells of *Escherichia coli* containing the vector plasmid pKK223-3 (lane 1) or recombinant plasmid pKVE14 (lane 2); Also shown are reactions against disrupted and centrifuged whole cells of *E. coli* (wpKE14) (lane 3) and further fractionation of V antigen by chromatography on phehyl-Sepharose CL-4B (lane 4), DEAE (diethylaminothyl) cellulose (lane 5), Sephacryl S-300SF (lane 6), calcium hydroxylapatite (lane 7), and a second passage on DEAE cellulose (lane 8).
Figure 7B:
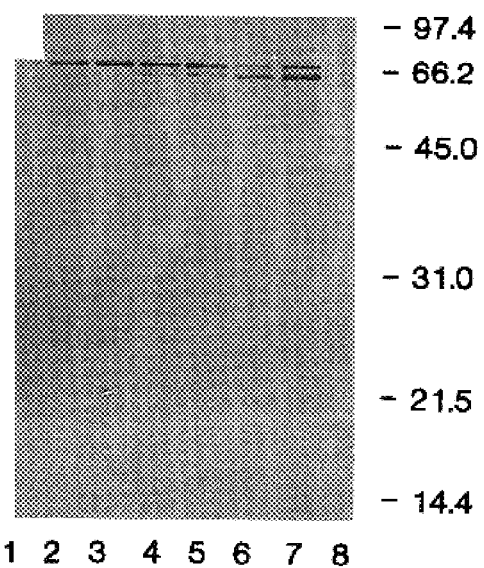

Passive Immunity Mediated by Anti-PAV. Preparations of homogenous γ-globulin were isolated from unabsorbed rabbit antisera raised against PA and PAV purified by affinity chromatography. Control anti-V antigen (FIGS. 4A and 4B) and anti-PAV (FIG. 4C), but not anti-PA (FIG. 4D), reacted with V antigens of all three *Yersinia* sp. High molecular weight antigens (ca. 70 kDa) common to both Lcr$^+$ and Lcr$^-$ yersiniae were recognized by both anti-PAV (FIG. 4C) and anti-PA (FIG. 4D). Anti-PAV (FIG. 7A) but not anti-PA (FIG. 7B) also identified the same degradation products of V antigen that were detected by the antisera characterized previously (FIG. 3). These findings verify that anti-PAV contains antibodies directed against epitopes unique to V antigen and provide further evidence that its degradation occurs at the C-terminal end.

Anti-PA and anti-PAV were tested for ability to confer passive immunity against intravenous infection with yersiniae. As shown in FIG. 5, anti-PA failed to provide protection whereas anti-PAV was highly effective against *Y. pestis* and *Y. pseudotuberculosis* but not *Y. enterocolitica*.

Discussion

Since its discovery, V antigen has been ascribed a role as protective antigen in conferring immunity to plague (8). Experimental evidence supporting this assumption was initially limited to the findings that active immunization with V antigen-rich fractions or passive immunization with antisera raised against such fractions provided protection against disease (23). The possibility thus remained that one or more additional antigens contributed to the immune state described by early workers. This concern was minimized upon introduction of preparative methods that permitted recovery of nearly homogenous V antigen (5). Nevertheless, antisera raised against lots purified by use of these procedures often contained antibodies directed against highly antigenic contaminating proteins, especially Yops, present at trace levels in the final product used for immunization. Although these antibodies were readily removed by absorption with cross-reacting material, this process necessitated introduction of bacterial macromolecules including lipopolysaccharide that might stimulate nonspecific resistance to infection. To minimize this possibility, it became necessary to purify the γ-globulin from absorbed antisera (40,62).

Concerns that these precautions, undertaken to assure monospecificity of anti-V antigen, had inadvertently introduced uncontrolled variables were largely eliminated by use of γ-globulin purified from antisera raised against highly purified V antigen cloned in *E. coli*. However, this process was also unsatisfactory due to the occurrence of marked degradation throughout the course of purification. As a result, only a fraction of the final product consisted of the 37 kDa primary lcrV product. Although γ-globulin purified from unabsorbed antiserum raised against this mixture provided satisfactory passive immunity, yields of antigenic material were insufficient to permit widespread immunization. The observation that cloned V antigen expressed in the protease-deficient background of *E. coli* BL21, like native V antigen purified from *Y. pestis*, underwent marked degradation during purification further suggests but does not prove that this process is autocatalytic.

Problems concerning specificity and degradation were resolved upon development of the fusion protein PAV that could be isolated at high yield as a homogenous stable protein in a single step. Antisera raised against PAV were somewhat more effective in providing protection against *Y. pestis*, and especially *Y. pseudotuberculosis* than was anti-recombinant V antigen. This finding emphasizes that passive immunity mediated by anti-V antigen does not require interaction with N-terminal epitopes because the latter were absent in PAV. The independent observation that the N-terminal end of V antigen was poorly antigenic (37) is consistent with this conclusion.

Detailed information with respect to the drawing figures is as follows.

FIG. 1. Scheme of construction of recombinant plasmid of pPAV13 encoding staphylococcal protein A-V antigen fusion protein (PAV) (A) and characterization of PAV (B). Sites of restriction endonuclease attack are designated; Ap and Cm are locations of markers of resistance for ampicillin and chloramphenicol, respectively. Lac designates the position of lacZ which provides selection of recombinant plasmids in the vector pBluescript SK+. The genes lcrG, lcrv, and lcrH comprise a portion of the lcrGVH-yopBD operon of *Yersinia pseudotuberculosis* 995 (38) and the designation Protein A is the truncated Protein A gene of *Staphylococcus aureus*. The dark arrows in A represent the hybrid gene encoding PAV shown in B to consist of the signal sequence (S), IgG-binding domains (E to B), the defective domain C' that has lost the ability to bind IgG, and truncated V antigen that has lost the first 67 amino acids of its N-terminal portion. Molecular weights in Kilodaltons are designated for each peptide arising after hydrolysis of the acid-labile Asp-Pro cleavage sites marked by arrowheads (60).

Figure 2:
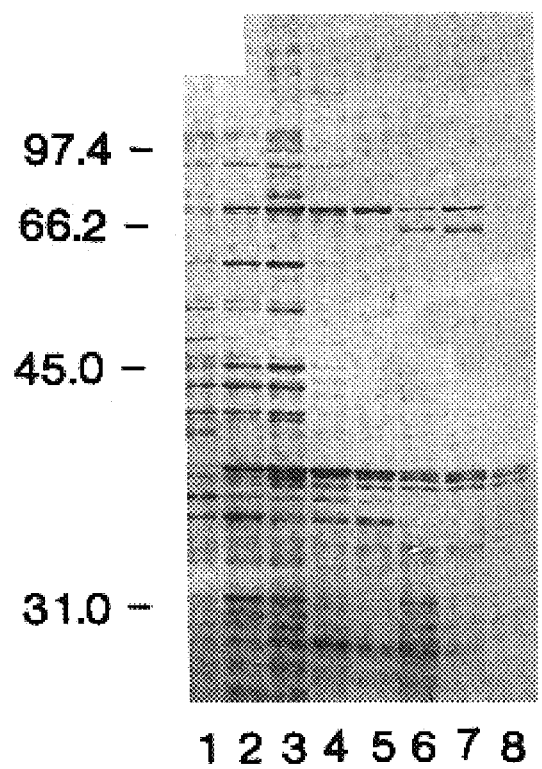
FIG. 2 is a silver-stained extended SDS gel of whole cells of *E. coli* BL 21 containing the vector plasmid pKK223-3 (lane 1) or recombinant plasmid pKVE14 (lane 2)

FIG. 2. Silver-stained 12.5% extended sodium dodecyl sulfate-polyacrylamide electrophoresis gel of whole cells of *Escherichia coli* BL21 containing the vector plasmid pKK223-3 (lane 1) or recombinant plasmid pKVE14 (lane 2). Whole cells of *E. coli* (pKVE14) were disrupted and centrifuged to prepare a cell-free extract (lane 3) that was fractionated by chromatography on phenyl-Sepharose CL-4B (lane 4), DEAE cellulose (lane 5), Sephacryl S-300SF (lane 6), calcium hydroxylapatite (lane 7), and a second passage on DEAE cellulose (lane 8). Note the presence of V antigen in lanes 2 through 8 as a major peptide of 37 kDa.

FIG. 3. Immunoblots prepared with rabbit polyclonal anti-V antigen (A), mouse monoclonal anti-V antigen 15A4.8 (B), and mouse monoclonal anti-V antigen 3A4.1 (C) directed against whole cells of *Escherichia coli* containing the vector plasmid pKK223-3 (lane 1) or recombinant plasmid pKVE14 (lane 2). Also shown are reactions against disrupted and centrifuged whole cells of *E. coli* (pKVE14) (lane 3) and further fractionation of V antigen by chromatography on phenyl-Sepharose CL-4B (Lane 4), DEAE cellulose (lane 5), Sephacryl S-300SF (lane 6), calcium hydroxylapatite (lane 7) and a second passage on DEAE cellulose (lane 8).

FIG. 4. Immunoblots prepared with rabbit anti-native V antigen purified from *Y. pestis* KIM (A), anti-recombinant V antigen (B), anti-protein A-V antigen fusion protein (C), and anti-Protein A (D) directed against $Ca^{2+}$-starved whole Lcr$^-$ cells of *Y. pestis* KIM (lane 1), Lcr$^+$ cells of *Y. pestis* KIM (lane 2), Lcr$^-$ cells of *Y. pseudotuberculosis* PB1 (lane 3), Lcr$^+$ cells of *Y. pseudotuberculosis* PB1 (lane 4), Lcr$^-$ cells of *Y. enterocolitica* WA (lane 5), and Lcr$^+$ cells of *Y. enterocolitica* WA (lane 6).

FIG. 5. Ability of 0.033 M potassium phosphate buffer, pH 7.0 (None) or control antiserum raised against native V antigen and experimental antisera raised against recombinant V antigen, protein A-V antigen fusion peptide, and recombinant protein A to provide passive protection in mice against 10 minimum lethal doses of Lcr$^+$ cells of *Yersinia pestis* KIM, *Yersinia pseudotuberculosis* PB1, and *Yersinia enterocolitica* WA. Mice were challenged intravenously and γ-globulins were then administered intravenously on postinfection days 1, 3, and 5 at, unless indicated otherwise, a dose of 100 μg. Lengths of solid bars show survival in days of individual mice eventually succumbing to infection; open bars represent survival of independent infected mice until the experiment was terminated at 21 days. Numbers adjacent to solid bars show mean survival time in days.

FIG. 6. Immunoblots prepared with rabbit anti-native V antigen (A) or mouse monoclonal 17A5.1 anti-V antigen (B) directed against truncated protein A (PA) (lane 1), protein A-V antigen fusion peptide (PAV) (lane 2), PAV partially hydrolyzed by formic acid (lane 3), PAV partially hydrolyzed by formic acid and passed through the IgG Sepharose 6FF column (lane 4), whole Lcr$^+$ cells of *Yersinia pestis* KIM (lane 5), and whole Lcr$^-$ cells of *Y. pestis* KIM (lane 6); A-V$_d$, V$_o$, V$_d$, and A indicate the positions of PAV, native V antigen (37 kDa), truncated V antigen (29.5 kDa), and truncated Protein A, respectively. Human γ-globulin was used to block nonspecific reactions of monoclonal antibodies against IgG binding domains of Protein A (26).

FIG. 7. Immunoblots prepared with rabbit anti-protein A-V antigen fusion peptide (A) and anti-truncated protein A (B) directed against whole cells of *Escherichia coli* containing the vector plasmid pKK223-3 (lane 1) or recombinant plasmid pKVE14 (lane 2). Also shown are reactions against disrupted and centrifuged whole cells of *E. coli* (pKVE14) (lane 3) and further fractionation of V antigen by chromatography on phenyl-Sepharose CL-4B (lane 4), DEAE cellulose (lane 5), Sephacryl S-300SF (lane 6), calcium hydroxylapatite (lane 7), and a second passage on DEAE cellulose (lane 8).

While the forms of the invention herein disclosed constitute presently preferred embodiments, many others are possible. It is not intended herein to mention all of the possible equivalent forms or ramifications of the invention. It is understood that the terms used herein are merely descriptive rather than limiting, and that various changes may be made without departing from the spirit or scope of the invention.

References

1. Bergman, T., S. Hakanseon, A. Forsberg, L. Norlander, A. Macellaro, A. Backman, I. Bolin, and H. Wolf-Watz. 1991. Analysis of the V antigen lcrGVH-yopBD operon of *Yersinia pseudotuberculosis*: Evidence for a regulatory role of LcrH and LcrV. J. BACTERIOL. 173:1607–1616.
2. Bolin, I., and H. Wolf-Watz. 1988. The virulence plasmid-encoded Yop2b protein of *Yersinia pseudotuberculosis* is a virulence determinant regulated by calcium and temperature at transcriptional level. MOL. MICROBIOL. 2:237–245.
3. Brubaker, R. R. 1991. The V antigen of yersiniae—an overview. CONTRIB. MICROBIOL. IMMUNOL. 12:127–133.
4. Brubaker, R. R. 1991. Factors promoting acute and chronic diseases caused by yersiniae. CLIN. MICROBIAL. Rev. 4:309–324.
5. Brubaker, R. R., A. K. Sample, D.-Z. Yu, R. J. Zahorchak, P. C. Hu, and J. M. Fowler. 1987. Proteolysis of V antigen from *Yersinia pestis*. MICROB. PATHOG. 2:49–62.
6. Burrows, T. W. 1956. An antigen determining virulence in *Pasteurella pestis*. Nature (London) 177:426–427.
7. Burrows, T. W., and G. A. Bacon. 1956. The basis of virulence in *Pasteurella pestis*: an antigen determining virulence. BRIT. J. EXP. PATHOL. 37-481–493.
8. Burrows, T. W., and G. A. Bacon. 1958. The effects of loss of different virulence determinants on the virulence and immunogenicity of strains of *Pasteurella pestis*. BRIT. J. EXP. PATH. 39:278–291.
9. Burrows, T. W., and G. A. Bacon. 1960. V and W antigens in strains of *Pasteurella pseudotuberculosis*. BR. J. EXP. PATHOL. 41:38–44.
10. Carter, P. B., R. J. Zahorchak, and R. R. Brubaker. 1980. Plague virulence antigens from *Yersinia enterocolitica*. INFECT. IMMUN. 28:638–640.
11. Charnetzky, W. T., and R. R. Brubaker. 1982. RNA synthesis in *Yersinia pestis* during growth restriction in calcium deficient medium. J. BACTERIOL. 149:1089–1095.
12. Cornelis, G., J.-C. Vanootegem, and C. Sluiters. 1987. Transcription of the yop regulon from *Y. enterocolitica* requires trans-acting pYV and chromosomal genes. MICROBIOL. PATH. 2:367–379.
13. Ferber, D. M., and R. R. Brubaker. 1981. Plasmids in *Yersinia pestis*. INFECT. IMMUN. 31:839–841.
14. Fetherston, J. D., P. Schuetze, and R. D. Perry. 1992. Loss of the pigmentation phenotype in *Yersinia pestis* is due to the spontaneous deletion of 102 kb of chromosomal DNA which is flanked by a repetitive element. MOL. MICROBIOL. 6:2693–2704.
15. Forsberg, A., A.-M. Vutanen, M. Skurnik, and H. Wolf-Watz. 1991. The surface-located YopN protein is involved in calcium signal transduction in *Yersinia pseudotuberculosis*. MOL. MICROBIAL. 5:977–986.
16. Gandecha, A. R., M. R. L. Owen, B. Cockburn, and G. C. Shitelam. 1992. Production and secretion of a bifunctional staphylococcal protein A::antiphytochrome single-chain Fv fusion protein in *Escherichia coli*. GENE 122:361–365.
17. Grodberg, J., and J. J. Dunn. 1988. ompT encodes the *Escherichia coli* outer membrane protease that cleaves T7 RNA polymerase during purification. J. BACTERIOL. 170:1245–1253.
18. Guan K., and J. E. Dixon. 1990. Protein tyrosine phosphatase activity of an essential virulence in *Yersinia*. SCIENCE 249:553–556.
19. Hakansson, S., T. Bergman, J.-C. Vanooteghem, G. Cornelis, and H. Wolf-Watz. 1993 YopB and YopD constitute a novel class of *Yersinia* Yop proteins. INFECT. IMMUN. 61:71–80.
20. Jackson, S., and T. W. Burrows. 1956. The pigmentation of *Pasteurella pestis* on defined medium containing haemin. BRIT. J. EXP. PATHOL. 37:570–576.
21. Jackson, S., and T. W. Burrows. 1956. The virulence enhancing effect of iron on non-pigmented mutants of virulent strains of *Pasteurella pestis*. BRIT. J. EXP. PATHOL. 37:577–583.
22. Kutyrev, V. V., A. A. Filippov, A. V. Drozdov, and O. A. Protsenko. 1988. Molecular cloning of the locus determining the synthesis of V antigen and its use to characterize the deletion derivatives of *Yersinia pestis* plasmid pCad, p. 3–11. In A. V. Naumov (ed.), Microbiology and biochemistry of particularly dangerous infections. Anti-Plague Institute "Microbe" Press, Saratov (In Russian).
23. Lawton, W. D., R. L. Erdman, and M. J. Surgalla. 1963. Biosynthesis and purification of V and W antigen in *Pasteurella pestis*. J. IMMUNOL. 91:179–184.
24. Leung, K. Y., B. S. Reisner, and S. C. Straley. 1990. Yop M inhibits platelet aggregation and is necessary for virulence of *Yersinia pestis* in mice. INFECT. IMMUN. 58:3262.
25. Leung, K. Y., and S. C. Straley. 1989. The YopM gene of *Yersinia pestis* encodes a released protein having homology with the human platelet surface protein GPIb_. J. BACTERIOL. 171:4623–4632.
26. Lowenadler, B., B. Jansson, S. Paleus, E. Lolmgren, B. Nilsson, T. Moks, G. Palm, S. Josephson, L. Philipson, and M. Uhlen. 1987. A gene fusion system for generating antibodies against short peptides. GENE 58:87–97.
27. Lowry, O. H., N. J. Rosebrough, A. L. Farr, and R. J. Randall. 1951. Protein measurement with the folin phenol reagent. J. BIOL. CHEM. 193:265–275.
28. Lucier, T. A., and R. R. Brubaker. 1992. Determination of genome size, macrorestriction pattern polymorphism, and nonpigmentation-specific deletion in *Yersinia pestis* by pulsed-filed gel electrophoresis. J. BACTERIOL. 174:2078–2086.
29. Maniatis, T., E. F. Fritsch, and J. Sambrook. 1982. Molecular cloning. Cold Spring Harbor Lab., Cold Spring Harbor, N.Y.
30. Mehigh, R. J. and R. R. Brubaker. 1993. Major stable peptides of *Yersinia pestis* synthesized during the low-calcium response. INFECT. IMMUN. 61:13–22.
31. Mehigh, R. J., A. K. Sample, and R. R. Brubaker. 1989. Expression of the low-calcium response in *Yersinia pestis*. MICROB. PATHOG. 6:203–217.

32. Michiels, T., and G. Cornelis. 1988. Nucleotide sequence and transcription analysis of yop51 from *Yersinia enterocolitica* W22703. MICROB. PATHOG. 5:449–459.

33. Michiels, T., and G. Cornelis. 1991. Secretion of hybrid proteins by the Yersinia Yop export system. J. BACTERIOL. 173:1677–1685.

34. Michiels, T., J.-C. Vanoolg hem, C. Lambert de Rouvroit, B. China, A. Gustin, P. Broudry, and G. Cornelis. 1991. Analysis of virC, an operon involved in the secretion of Yop proteins by *Yersina enterocolitica*. J. BACTERIOL. 173:4994–5009.

35. Michiels, T., P. Wattiau, R. Brasseur, J.-M. Ruysschaert, and G. Cornelis. 1990. Secretion of Top proteins by Yersiniae. INFECT. IMMUN. 58:2840–2849.

36. Morrisey, J. H. 1981. Silver stain for proteins in polyacrylamide gels: a modified procedure with enhanced uniform sensitivity. ANAL. BIOCHEM. 117:307–310.

37. Motin, V. L., R. Nakajima, G. B. Smirnov, and R. R. Brubaker. 1993. Effect of deletions within lcrV on expression of passive immunity mediated by anti-V antigen. INFECT. IMMUN. (Submitted).

38. Motin, V. L., M. S. Pokrovskaya, M. V. Telepnev, V. V. Kutyrev, N. A. Vidyaeva, A. A. Filippov, and G. B. Smirnov. 1991. The difference in the lcrV-sequences between *Y. pestis* and *Y. pseudotuberculosis* and its application for characterization of *Y. pseudotuberculosis* strains. MICROB. PATHOG. 12:165–175.

39. Mulder, B., T. Michiels, M. Simonet, M. Sory, and G. Cornelis. 1989. Identification of additional virulence determinants of the pYV plasmid of *Yersinia enterocolitica* W227. INFECT. IMMUN. 57:2534–2541.

40. Nakajima, R., and R. R. Brubaker. 1993. Association between virulence of *Yersinia pestis* and suppression of gamma interferon and tumor necrosis factor alpha. INFECT. IMMUN. 61:23–31.

41. Nilsson, B., L. Abrahmsen, and M. Uhlen. 1985. Immobilization and purification of enzymes with staphylococcal protein A gene fusion vectors. EMBO J. 4:1075–1080.

42. Nilsson, B., E. Holgren, S. Josephson, S. Gatenbeck, L. Philipson, and M. Uhlen. 1985. Efficient secretion and purification of human insulin-like growth factor T with a gene fusion vector in Staphylococci. NUCL. ACIDS RES. 13:1151–1162.

43. Perry, R. D., and R. R. Brubaker. 1983. Vwa$^+$ phenotype of *Yersinia enterocolitica*. INFECT. IMMUN. 40:166–171.

44. Perry, R. D., P. A. Harmon, W. S. Bowmer, and S. C. Straley. 1986. A low-Ca$^{2+}$ response operon encodes the V antigen of *Yersinia pestis*. INFECT. IMMUN. 54:428–434.

45. Price, S. B., C. Cowan, R. D. Perry, and S. C. Straley. The V antigen is a regulator protein necessary for the Ca$^{2+}$-dependent growth and the maximal expression of low-Ca$^{2+}$ response virulence genes in *Yersinia pestis*. J. BACTERIOL. 173:2649.

46. Price. S. B., K. Y. Leung, S. S. Barve, and S. C. Straley. 1989. Molecular analysis of lcrGVH, the V operon of *Yersinia pestis*. J. BACTERIOL. 171: 5646–5653.

47. Reisner, B. S., and S. C. Straley. 1992. *Yersinia pestis* YopM: Thrombin binding and overexpression. INFECT. IMMUN. 60:5242–5252.

48. Rosqvist R., I. Bolin, and H. Wolf-Watz. 1988. Inhibition of phagocytosis in *Yersinia pseudotuberculosis*: a virulence plasmid-encoded ability involving the Yop2b protein. INFECT. IMMUN. 56:2139–2143.

49. Rosqvist, R., A. Forsberg, M. Rempelain n, T. Bergman, and H. Wolf-Watz. 1990 The Cytotoxic Yop E of *Yersinia* obstructs the primary host defense. MOL. MICROBIAL. 4:657.

50. Rosqvist, R., A. Forsberg, and H. Wolf-Watz. 1991. Intracellular targeting of the Yersinia YopE cytotoxin in mammalian cells induces actin microfilament disruption. INFECT. IMMUN. 59:4562–4569.

51. Sample, A. K., J. M. Fowler, and R. R. Brubaker. 1987. Modulation of the low calcium response in *Yersinia pestis* by plasmid-plasmid interaction. MICROB. PATHOG. 2:443–453.

52. Sample A. K., and R. R. Brubaker. 1987. Posttranslational regulation of Lcr plasmid-mediated peptides in pesticinogenic *Yersinia pestis*. MICROB. PATHOG. 3:239–248.

53. Sato, K., R. Nakamima, F. Hara, T. Une, and Y. Osada. 1991. Preparation of monoclonal antibody to V antigen from *Yersinia pestis*. CONTRIB. MICROBIOL. IMMUNOL. 12:225–229.

54. Sodeinde, O. A., A. K. Sample, R. R. Brubaker, and J. D. Goguen. 1988. Plasminogen activator/coagulase gene of *Yersinia pestis* is responsible for degradation of plasmid-encoded outer membrane proteins. INFECT. IMMUN. 56:2749–2752.

55. Sodeinde, O. A., Y. V. B. K. Subrahamanyam, K. Stark, T. Quan, Y. Bao, and J. D. Goguen. 1992. A surface protease and the invasive nature of plague. SCIENCE 258:1004–1007.

56. Straley, S. C., and W. S. Bowmer. 1986. Virulence genes regulated at the transcriptional level by Ca$^{2+}$ in *Yersinia pestis* include structural genes for outer membrane proteins. INFECT. IMMUN. 51:445–454.

57. Straley, S. C., and R. R. Brubaker. 1982. Localization in *Yersinia pestis* of peptides associated with virulence. INFECT. IMMUN. 36:129–135.

58. Straley, S. C., and M. L. Cibull. 1989. Differential clearance and host-pathogen interactions of YopE$^-$ and YopK$^-$ YopL$^-$ *Yersinia pestis* in BALB/c mice. INFECT. IMMUN. 57:1200–1210.

59. Surgalla, M. J. and E. D. Beesley. 1969. Congo redagar plating medium for detecting pigmentation in *Pasteurella pestis*. APPL. MICROBIOL. 18:834–837.

60. Uhlen, M., B. Guss, B. Nilsson, S. Gatenbeck, L. Philipson, and M. Lindberg. 1984. Complete sequence of the staphylococcal gene encoding protein A. J. BIOL. CHEM. 259:1695–1702.

61. Une, T., and R. R. Brubaker. 1984 In vivo comparison of avirulent Vwa$^-$ and Pgm or Pst$^r$ phenotypes of yersiniae. INFECT. IMMUN. 43:895–900.

62. Une, T., and R. R. Brubaker. 1984. Roles of V antigen in promoting virulence and immunity in yersiniae. J. IMMUNOL. 133:2226–2230.

63. Une, T., R. Nakajima, and R. R. Brubaker. 1986. Roles of V antigen in promoting virulence in Yersinia. CONTRIB. MICROBIOL. IMMUNOL. 9:179–185.

64. Zahorchak, R. J., W. T. Charnetzky, R. V. Little, and R. R. Brubaker. 1979. Consequences of Ca$^{2+}$ deficiency on macromolecular synthesis and adenylate energy charge in *Yersinia pestis*. J. BACTERIOL. 139:792–799.

What is claimed is:

1. An isolated and purified recombinant V antigen encoded by the plasmid construct pPAV13 as shown in FIG. 1.

2. An isolated and purified recombinant V antigen lacking the first 67 N-terminal amino acids of native V antigen.

3. The isolated and purified recombinant V antigen of claim 1, wherein the plasmid comprises low calcium response regions V and H and the structural gene for staphylococcal protein A.

* * * * *